United States Patent
Kim et al.

[11] Patent Number: 6,010,974
[45] Date of Patent: Jan. 4, 2000

[54] CARBON AND/OR SILICON BRIDGED BINUCLEAR METALLOCENE CATALYST FOR STYRENE POLYMERIZATION

[75] Inventors: Hyun-Joon Kim; Yi-yeol Lyu; Dong-ho Lee, all of Daejeon, Rep. of Korea

[73] Assignee: Cheil Industries, Inc., Kumee, Rep. of Korea

[21] Appl. No.: 08/844,109

[22] Filed: Apr. 28, 1997

[30] Foreign Application Priority Data

Mar. 7, 1997 [KR] Rep. of Korea .................. 97-7660

[51] Int. Cl.⁷ ................. B01J 31/00; C07F 7/00; C07F 7/28; C07F 17/00
[52] U.S. Cl. .............. 502/152; 502/153; 502/155; 502/156; 502/158; 502/103; 502/117; 526/11; 526/12; 526/52; 526/53; 526/160; 526/943
[58] Field of Search ................ 556/11, 12, 52, 556/53; 502/152, 153, 155, 156, 158, 103, 117

[56] References Cited

U.S. PATENT DOCUMENTS

| | | | |
|---|---|---|---|
| 3,426,053 | 2/1969 | Rosenberg | 556/11 |
| 3,849,459 | 11/1974 | Maitlis et al. | 502/155 |
| 4,024,169 | 5/1977 | Pez | 556/53 |
| 4,361,497 | 11/1982 | Boldt et al. | 502/153 |
| 5,372,980 | 12/1994 | Davis | 502/103 |
| 5,585,508 | 12/1996 | Kuber et al. | 502/153 |
| 5,627,117 | 5/1997 | Mukaiyama et al. | 502/103 |
| 5,770,666 | 6/1998 | Hamura et al. | 556/53 |
| 5,770,755 | 6/1998 | Schertl et al. | 556/53 |
| 5,807,938 | 9/1998 | Kaneko et al. | 502/152 |
| 5,880,302 | 3/1999 | Hermann et al. | 502/153 |
| 5,892,079 | 4/1999 | Wilson, Jr. | 556/12 |

FOREIGN PATENT DOCUMENTS

| | | |
|---|---|---|
| 0 210 615 | 2/1987 | European Pat. Off. |
| 0 530 908 | 3/1993 | European Pat. Off. ............... 556/53 |
| 1 153 749 | 9/1963 | Germany ................ 556/53 |
| 59-25310 | 2/1984 | Japan .................. 556/52 |
| 63-191811 | 8/1988 | Japan . |
| 3-250007 | 11/1991 | Japan . |
| 3-258812 | 11/1991 | Japan . |
| 4-275313 | 9/1992 | Japan . |
| 5-105712 | 4/1993 | Japan . |
| WO 92/15596 | 9/1992 | WIPO ................... 556/53 |

OTHER PUBLICATIONS

H. Brintzinget et al., J. Am. Chem. Soc., vol. 92, No. 21, pp. 6182–6185, Oct. 1970.
G. Pez et al., J. Am. Chem. Soc., vol. 101, No. 23, pp. 6933–6937, Nov. 1979.

*Primary Examiner*—Mark L. Bell
*Assistant Examiner*—J. Pasterczyk
*Attorney, Agent, or Firm*—Staas & Halsey LLP

[57] ABSTRACT

An alkylene and/or silylene bridged binuclear metallocene catalyst for styrene polymerization is represented by the following formula (I):

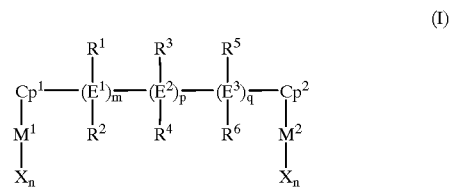

where $M^1$ and $M^2$ are the same or different transition metal of Group IVb of the Periodic Table; $Cp^1$ and $Cp^2$ are the same or different cyclopentadienyl; alkyl, alkoxy, silyl or halogen substituted cyclopentadienyl; indenyl; alkyl, alkoxy, silyl or halogen substituted indenyl; fluorenyl; or alkyl, alkoxy, silyl or halogen substituted fluorenyl, which is capable of π-electron, $\eta^5$-bonding with $M^1$ or $M^2$; each of $E^1$, $E^2$ and $E^3$, independently of one another, is a carbon atom or a silicon atom; m, p and q are integers of 0 to 15 and $m+p+q \geq 1$; each of $R^1$, $R^2$, $R^3$, $R^4$, $R^5$ and $R^6$, independently of one another, is a hydrogen, an alkyl, an aryl, an alkoxy or a halogen; X is a hydrogen, an alkyl, an alkoxy or a halogen; and n is 3. $M^1$ and $M^2$ may also be in cardin form by mixture of (I) with a compound which abstracts an X gray from each metal atom and substitution then with non-coordinating anions.

10 Claims, No Drawings

CARBON AND/OR SILICON BRIDGED BINUCLEAR METALLOCENE CATALYST FOR STYRENE POLYMERIZATION

FIELD OF THE INVENTION

The present invention relates to carbon and/or silicon bridged binuclear metallocene catalysts for polymerization of styrene. More particularly, the present invention relates to alkylene bridged binuclear metallocene (ABBM) catalysts, silylene bridged binuclear metallocene (SBBM) catalysts and alkylene-silylene bridged binuclear metallocene (A-SBBM) catalysts for preparing a syndiotactic polystyrene, and to methods for preparing the catalysts. The present invention also includes a process for preparing a syndiotactic polystyrene using the ABBM, SBBM or A-SBBM catalyst through homopolymerization, copolymerization or terpolymerization of styrene.

BACKGROUND OF THE INVENTION

A number of metallocene catalysts have been developed and widely used for preparing a polystyrene having high stereoregularity or a polyolefin having good physical properties. The conventional metallocene catalysts have a sandwich type structure comprising a compound of a transition metal of Group IVb of the Periodic Table and a ligand having one or two cycloalkanedienyl groups such as cyclopentadienyls, indenyls and fluorenyls. The metallocene catalysts are usually employed with a co-catalyst in a polymerization process. An illustrative co-catalyst is an alkylaluminoxane, i.e., methylaluminoxane, which is a reaction product of an alkylaluminum compound with water. Syndiotactic or isotactic polystyrenes having stereoregularity can be produced by using the metallocene catalysts. In this area of stereotype polystyrenes, syndiotactic polystyrenes alternatively having benzene rings on the main chain of the polymers are significant in that the polymers have excellent physical properties such as heat resistance, since the polymers have a melting point ($T_m$) of about 270° C. due to more stereoregularity than amorphous isotactic polystyrenes.

European Patent Publication No. 210 615 A2 discloses a styrene polymer having stereoregularity and metallocene catalysts such as cyclopentadienyl trichlorotitanes and alkyl-substituted cyclopentadienyl trichlorotitanes. It is known that the metallocene catalysts of the European Patent have good catalyst activity, molecular weight distribution and syndiotactic index.

Japanese Patent Laid-Open Nos. 63-191811 and 03-250007 disclose a sulfur bridged metallocene catalyst. However, the catalyst has a disadvantage in that the yield of the catalyst is very low. Although various alkyl bridged metallocene catalysts are disclosed in Japanese Laid-Open Nos. 03-258812, 04-275313 and 05-105712, the metallocene catalysts are disadvantageous in low yield of the catalysts.

In order to overcome the shortcomings of the conventional metallocene catalysts, the present inventors have developed alkylene bridged binuclear metallocene (ABBM) catalysts, silylene bridged binuclear metallocene (SBBM) catalysts and alkylene-silylene bridged binuclear metallocene (A-SBBM) catalysts for preparing a syndiotactic polystyrene, method for preparing the catalysts, and a process for preparing syndiotactic polystyrene using the catalysts.

OBJECTS OF THE INVENTION

An object of this invention is to provide an alkylene and/or silylene bridged binuclear metallocene catalyst having a good catalyst activity for polymerization of styrene.

Another object of the invention is to provide an alkylene and/or silylene bridged metallocene catalyst for preparing a syndiotactic polystyrene having a high stereoregularity, a high melting point, a high crystallizing temperature, and a good molecular weight distribution.

A further object of the invention is to provide a process for preparing an alkylene and/or silylene bridged binuclear metallocene catalyst for polymerization of styrene.

A still further object of the invention is to provide a process for preparing a syndiotactic polystyrene using the alkylene and/or silylene bridged binuclear metallocene catalyst through homopolymerization, copolymerization or terpolymerization of styrene.

These and other objects and advantages may be found in various embodiments of the present invention. It is not necessary that each and every object or advantage be found in all embodiments of the present invention. It is sufficient that the present invention may be advantageously employed.

Other objects and advantages of this invention will be apparent from the ensuing disclosure and appended claims.

SUMMARY OF THE INVENTION

The carbon and/or silicon bridged binuclear metallocene catalyst according to the present invention has a sandwich type structure in which same or different two compounds selected from the group consisting of an $\eta^5$-bonding, $\pi$-electron cyclopentadienyl; an alkyl, alkoxy, silyl or halogen substituted cyclopentadienyl; and indenyl; an alkyl, alkoxy, silyl or halogen substituted indenyl; a fluorenyl; and an alkyl, alkoxy, silyl or halogen substituted fluorenyl, which are bonded to a transition metal of Group IVb of the Periodic Table, are bridged with an alkylene compound, a silylene compound or an alkylene-silylene compound. The metallocene catalyst includes a neutral compound of the catalyst and a cationic compound of the catalyst.

The carbon and/or silicon bridged binuclear metallocene catalyst according to the present invention is prepared by (1) providing an alkali metal compound of an $\eta^5$-bonding, $\pi$-electron cyclopentadienyl; an alkyl, alkoxy, silyl or halogen substituted cyclopentadienyl; an indenyl; an alkyl, alkoxy, silyl or halogen substituted indenyl; a fluorenyl; and an alkyl, alkoxy, silyl or halogen substituted fluorenyl, (2) reacting the alkali metal compound with an alkylene compound, a silyl compound or an alkylene-silylene compound, thereby producing an alkyl bridged compound, a silylene bridged compound or an alkylene-silylene bridged compound of same or different two groups of a cyclopentadienyl; an alkyl, alkoxy, silyl or halogen substituted cyclopentadienyl; an indenyl; an alkyl, alkoxy, silyl or halogen substituted indenyl; a fluorenyl; and an alkyl, alkoxy, silyl or halogen substituted fluorenyl, (3) reacting the bridged compound with an alkali metal or thallium compound having an alkyl or alkoxy group, thereby producing a salt state compound of the bridged compound, and (4) reacting the salt state compound of the bridged compound with a transition metal compound of Group IVb of the Periodic Table. In the method above, trimethylsilane or tert-butyl titanium can be added to the salt state compound of the bridged compound before the salt state compound is reacted with a transition metal compound.

The present invention also includes a process for preparing a syndiotactic polystyrene using the ABBM, SBBM or A-SBBM catalyst through homopolymerization, copolymerization or terpolymerization of styrene.

DETAILED DESCRIPTION OF THE INVENTION

The carbon and/or silicon bridged binuclear metallocene catalyst according to the present invention has a sandwich type structure in which same or different two compounds selected from the group consisting of an $\eta^5$-bonding, $\pi$-electron cyclopentadienyl; and alkyl, alkoxy, silyl or halogen substituted cyclopentadienyl; an indenyl; an alkyl, alkoxy, silyl or halogen substituted indenyl; a fluorenyl; and an alkyl, alkoxy, silyl or halogen substituted fluorenyl, which are bonded to a transition metal of Group IVb of the Periodic Table, are bridged with an alkyl compound, a silyl compound or an alkyl-silyl compound. The carbon and/or silicon bridged binuclear metallocene catalyst according to the present invention is represented by the following formula (I) or (II):

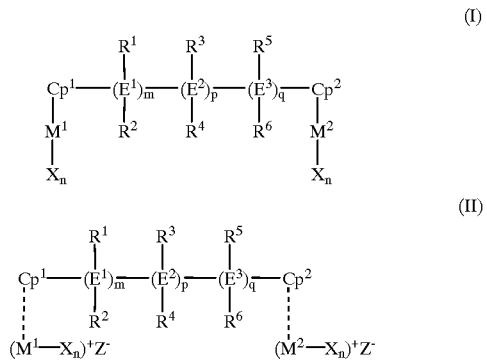

wherein $M^1$ and $M^2$ are the same or different transition metal of Group IVb of the Periodic Table such as titanium, zirconium or hafnium; $Cp^1$ and $Cp^2$ are the same or different cyclopentadienyl; alkyl, alkoxy, silyl or halogen substituted cyclopentadienyl; indenyl; alkyl, alkoxy, silyl or halogen substituted indenyl; fluorenyl; or alkyl, alkoxy, silyl or halogen substituted fluorenyl, which is capable of $\pi$-electron, $\eta^5$-bonding with $M^1$ or $M^2$; each of $E^1$, $E^2$ and $E^3$, independently of one another, is a carbon atom or a silicon atom; m, p and q are integers of 0 to 15 and $m+p+q \geq 1$; each of $R^1$, $R^2$, $R^3$, $R^4$, $R^5$ and $R^6$, independently of one another, is a hydrogen, an alkyl, an aryl, an alkoxy or a halogen; X is a hydrogen, an alkyl, an alkoxy or a halogen; n is 3; and Z is a non-coordinating anion represented by the formula $[BQ_1Q_2Q_3Q_4]^-$, where B is a boron having +3 valence, each of $Q_1$, $Q_2$, $Q_3$ and $Q_4$, independently of one another, is a radical selected from the group consisting of a hydride, a dialkylamido, an alkoxide, an aryl oxide and a hydrocarbyl.

The alkylene bridged binuclear metallocene (ABBM) catalysts, silylene bridged binuclear metallocene (SBBM) catalysts and alkylene-silylene bridged binuclear metallocene (A-SBBM) catalysts according to the present invention are prepared as set forth below.

The carbon and/or silicon bridged binuclear metallocene catalyst according to the present invention is prepared by (1) providing an alkali metal compound of an $\eta^5$-bonding, $\pi$-electron cyclopentadienyl; an alkyl, alkoxy, silyl or halogen substituted cyclopentadienyl; an indenyl; an alkyl, alkoxy, silyl or halogen substituted indenyl; a fluorenyl; and an alkyl, alkoxy, silyl or halogen substituted fluorenyl, (2) reacting the alkali metal compound with an alkylene compound, a silyl compound or an alkylene-silylene compound, thereby producing an alkyl bridged compound, a silylene bridged compound or an alkylene-silylene bridged compound of same or different two groups of a cyclopentadienyl; an alkyl, alkoxy, silyl or halogen substituted cyclopentadienyl; an indenyl; an alkyl, alkoxy, silyl or halogen substituted indenyl; a fluoroenyl; and an alkyl, alkoxy, silyl or halogen substituted fluorenyl, (3) reacting the bridged compound with an alkali metal or thallium compound having an alkyl or alkoxy group, thereby producing a salt state compound of the bridged compound, and (4) reacting the salt state compound of the bridged compound with a transition metal compound of Group IVb of the Periodic Table. In the method above, trimethylsilane or tert-butyl titanium can be added to the slat state compound of the bridged compound before the salt state compound is reacted with a transition metal compound.

In the first step, the alkali metal compound is an alkali metal-containing cyclopentadienyl, an alkali metal-containing indenyl, or an alkali metal-containing fluorenyl. The cyclopentadienyl, indenyl and fluorenyl include an alkali metal-containing cyclopentadienyl, an alkali metal-containing indenyl, and an alkali metal-containing fluorenyl, which are substituted with an alkyl, an alkoxy, a silyl or a halogen.

The alkali metal compound reacts with an alkylene compound, a silylene compound or an alkylene-silylene compound as in the following equation (III):

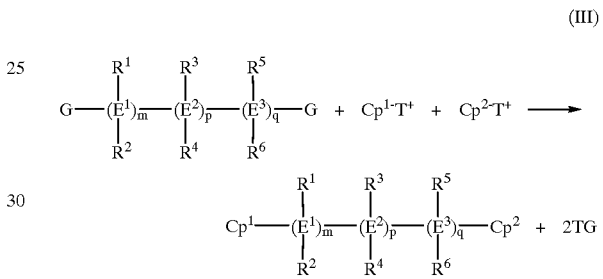

wherein G is a halogen atom such as fluorine, chlorine, bromine and iodine or a group selected from the group consisting of a methane sulfonyl, a benzene sulfonyl, a para-toluene sulfonyl and an acetyl, T is an alkali metal, and others are the same as defined above.

In case that $Cp^1$ and $Cp^2$ are different each other in the equation (III), $Cp^-T^+$ is reacted first and then $Cp^-T^+$ is reacted.

Illustrative examples of the alkylene compound in the equation (III) are dibromomethane, 1,2-dibromoethane, 1,3-dibromopropane, 1,4-dibromobutane, 1,5-dibromopentane, 1,6-dibromohexane, 1,7-dibromoheptane, 1,8-dibromooctane, 1,9-dibromononane, 1,10-dibromodecane, 1,11-dibromoundecane, 1,12-dibromododecane, 1,13-dibromotridecane, 1,14-dibromotetradecane and 1,15-dibromopentadecane. The bromine atom of the alkyl compounds may be substituted with a halogen of a fluorine, a chlorine and an iodine or a group selected from the group consisting of a methane sulfonyl, a benzene sulfonyl, a para-toluene sulfonyl and an acetyl.

Illustrative examples of the silylene compound in the equation (III) are chlorodimethyldisilane, dichloromethylsilane, dichlorosilane, 1,2-dichlorotetramethyldisilane, 1,3-dichlorohexsamethyldisilane, and 1,4-dichlorooctamethyldisilane. The chlorine atom of the silyl compounds may be substituted with a halogen of a fluorine, a bromine and an iodine or a group selected from the group consisting of a methane sulfonyl, a benzene sulfonyl, a para-toluene sulfonyl and an acetyl.

Illustrative examples of the alkylene-silylene compound in the equation (III) are 1,2-bis(chlorodimethylsilyl)ethane, 1,3-bis(chlorodimethylsilyl)-propane, 1,4-bis (chlorodimethylsilyl)butane, 1,5-bis(chlorodimethylsilyl)-pentane, 1,6-bis(chlorodimethylsilyl)hexane, 1,7-bis(chlorodimethylsilyl)-heptane, 1,8-bis(chlorodimethylsilyl) octane, 1,9-bis(chlorodimethylsilyl)-nonane, 1,10-bis (chlorodimethysilyl)decane, 1,11-bis(chlorodimethylsilyl)-undecane, 1,12-bis(chlorodimethylsilyl)dodecane, 1,13-bis (chlorodimethyl-silyl)tridecane, 1,14-bis(chlorodimethylsilyl)tetradecane, 1,15-bis (chlorodimethylsilyl)pentadecane, bis(chloromethyl) dimethylsilane, bis(chloroethyl)dimethylsilane, bis (chloropropyl)dimethylsilane, bis(chlorobutyl) dimethylsilane, bis(chloropentyl)dimethylsilane, bis (chlorobutyl)dimethylsilane, bis(chloropentyl) dimethylsilane, bis-(3-chloroethyl)dichlorosilane), bis-(3-chloropropyl)dichlorosilane, bis-3-chlorobutyl) dichlorosilane, bis-(3-chloropentyl)dichlorosilane, bis-(3-chlorohexyl)dichlorosilane, bis-(3)-chloroheptyl) dichlorosilane, bis-(3-chloroocytl)dichlorosilane, 1,2-bis (trichlorosilyl)ethane, 1,3-bis(trichlorosilyl)propane, 1,4-bis (trichlorosilyl)butane, 1,5-bis(trichlorosilyl)pentane, 1,6-bis (trichlorosilyl)hexane, 1,7-bis(trichlorosilyl)heptane, 1,8-bis (trichlorosilyl)octane, 1,9-bis(trichlorosilyl)octane and 1,10-bis(trichlorosilyl)decane. The chlorine atom of the alkylene-silylene compounds may be substituted with a fluorine, a bromine or an iodine.

The alkali metal compound in the following equation (III) is a ligand containing an alkali metal. Representative examples of the alkali metal compound are a Na-cyclopentadienide; an alkyl, alkoxy, silyl or halogen substituted Na-cyclopentadienide; a Na-indenide; an alkyl, alkoxy, silyl or halogen substituted Na-indenide; a Na-fluorenide; and an alkyl, alkoxy, silyl or halogen substituted Na-fluorenide. The natrium atom of the alkyl metal compound may be substituted with a lithium, a potassium or a thallium.

The reaction by equation (III) produces an alkylene bridged compound, a silylene bridged compound or an alkylene-silylene bridged compound of same or different two groups of a cyclopentadienyl; an alkyl, alkoxy, silyl or halogen substituted cyclopentadienyl; an indenyl; an alkyl, alkoxy, silyl or halogen substituted indenyl; a fluorenyl; and an alkyl, alkoxy, silyl or halogen substituted fluorneyl.

In the third step, the bridged compound reacts with an alkali metal or thallium compound having an alkyl or alkoxy group as in the following equation (IV):

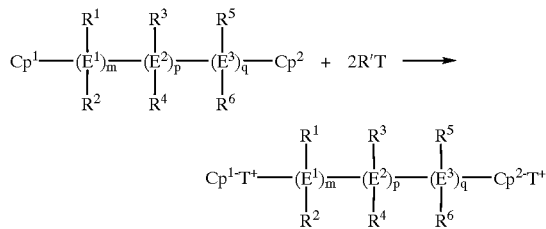

wherein R' is an alkyl or an alkoxy, and T is an alkali metal or a thallium. Representative Examples of the alkali metal or thallium compound having an alkyl or alkoxy group are a butyl lithium, a sec-butyl lithium, a tert-butyl lithium, a methyl lithium, a Na-methoxide, a Na-ethoxide and a thallium ethoxide.

The reaction by equation (IV) produces a salt state compound of an alkylene bridged compound, a silylene bridged compound or an alkylene-silylene bridged compound of same or different two groups of a cyclopentadienyl; an alkyl, alkoxy, silyl or halogen substituted cyclopentadienyl; an indenyl; an alkyl, alkoxy, silyl or halogen substituted indenyl; a fluorenyl; and an alkyl, alkoxy, silyl or halogen substituted fluorenyl.

In the fourth step, the salt state compound of the bridged compound reacts with a transition metal compound of Group IVb of the Periodic Table as in the following equation (V):

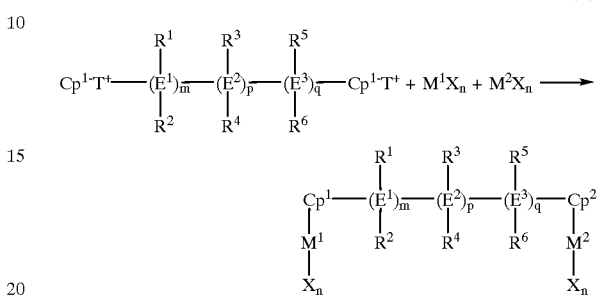

wherein $M^1$, $M^2$ and X are the same as defined above.

The transition metal compound of Group IVb of the Periodic Table in equation (V) is a compound in which a transition metal is bonded to one or more groups selected from the group consisting of a hydrogen, an alkyl, an aryl, a silyl, an alkoxy, an aryloxy, a siloxy and a halogen. Illustrative examples of the transition metal compound are titanium tetrachloride, zirconium tetrachloride and hafnium tetrachloride.

In case that $M^1$ and $M^2$ are different each other in the equation (V), $M^1X_n$ is reacted first and then $M^2X_n$ is reacted.

In the method above, trimethylsilane or tert-butyl titanium can be added to the salt state compound of the bridged compound before the salt state compound is reacted with a transition metal compound.

The product of the equation (V) is a binuclear metallocene catalyst represented by the general formula (I) above. The metallocene catalyst represented by the general formula (II) above is prepared by bonding a non-coordinating anion to the metallocene catalyst of the general formula (I).

The alkylene and/or silylene bridged binuclear metallocene catalyst of the general formula (I) or (II) is supported on a support for polymerization of styrene. In other words, the metallocene catalyst is supported on a dehydrated supporter. Exemplary supports are silica, alumina, magnesium chloride, zeolite, aluminum phosphate and zirconia. The support can be activated with a non-aluminum co-catalyst or an organometallic compound. Exemplary non-aluminum co-catalysts useful in this invention are $[R_7R_8R_9Cl]^+$ $[BQ_1Q_2Q_3Q_4]^-$ and $[HNR_{10}R_{11}R_{12}]^+[BQ_1Q_2Q_3Q_4]^-$, wherein $R_7 \sim R_{12}$, independently of one another, are a hydrogen, an alkyl, an aryl, an alkoxy, a silyl or a siloxy, B is a boron having +3 valence, and each of $Q_1$, $Q_2$, $Q_3$ and $Q_4$, independently of one another, is a radical selected from the group consisting of a hydride, a dialkylamido, an alkoxide, an aryl oxide and a hydrocarbyl. Exemplary organometallic compounds are an alkylaluminoxane or an organoaluminum compound. Illustrative examples of the alkylaluminoxane are a methylaluminoxane (MAO) and a modified methylaluminoxane (MMAO), and an illustrative example of the organoaluminum compound is $AlR_nX_{3-n}$, wherein R is an alkyl or aryl havig $C_1-C_{10}$, X is a halogen, and n is an integer of 1–3.

Syndiotactic polystyrene is prepared using an alkylene and/or silylene bridged binuclear metallocene catalyst of this invention. Syndioactic polystyrene is prepared using the ABBM, SBBM or A-SBBM catalyst of this invention through homopolymerization, copolymerization or terpolymerization of styrene. Homopolymerization of styrene means polymerization of styrene monomers or monomers of a styrene derivative. Examples of the styrene derivative usable in this invention are an α-methyl styrene, a para-methyl styrene, an α-chlorostyrene and a para-chlorostyrene. Copolymerization of styrene means polymerization of any two selected from styrene monomers, monomers of styrene derivatives, α-olefin monomers and polar monomers. Examples of the α-olefin monomers usable in this invention are an ethylene, a propylene, a butene, a butadiene, a polybutadiene, a hexene and an octene. Examples of the polar monomers are a methyl methacrylate (MMA), acrylonitrile (AN), vinylacetate (VA) and vinylchloride monomer (VCM). Terpolymerization of styrene means polymerization of any three monomers selected from styrene monomers, monomers of styrene derivatives, α-olefin monomers and polar monomers.

The catalyst is used in the amount of $10^{-7} \sim 10^{-3}$ mol per 1 l of solvent, preferably in amount of $10^{-6} \sim 10^4$ mole. The polymerization temperature is 0~100° C., preferably 30~60° C.

The invention may be better understood by reference to the following examples which are intended for purposes of illustration and are not to be construed as in any way limiting the scope of the present invention, which is defined in the claims appended hereto.

EXAMPLES

The following Examples 1–6 are carried out to prepare the catalysts in accordance with the present invention, the following Examples A–C are carried out to produce syndiotactic polystyrene using the catalysts of Examples 1–6, and the following Comparative Examples A1–A3, B1–B3 and C1–C3 are carried out to compare with Examples 1–6.

Examples 1–6

Representative catalysts of ABBM, SBBM and A-SBBM are prepared in the following manner.

Example 1: snythesis of butane-bis($\eta^5$-diindenyltitanium-trichloride): [IndTiCl$_3$-(CH$_2$)$_4$-IndTiCl$_3$]

After dissolving 10 mmole of 1,4-dibromobutane in 100 ml of tetrahydrofuran (THF), to the solution were added butyl lithium and indene to produce white powder. The white powder 20 mmole was dissolved in 50 ml of TMF at −78° C., the solution was heated at room temperature, and then agitated for about 30 hours. To the solution was added 200 ml of diethylether and 100 ml of water to prepare a greasy type reaction mixture. To the mixture was added 50 ml of hexane, and a white powder ligand that two indenes were bridged was obtained in 90% of yield. To 9 mmol of the ligand compound was added 50 ml of hexane, 18 mmol of butyl lithium was added at −78° C., the solution was heated at room temperature, and then agitated for about 5 hours. A white powder dianion compound in which two indenyls were bonded to lithium atoms was obtained. After filtering the dianion compound, trimethylsilylchloride (TMSCl) was added in 100 ml of hexane solvent, agitated for 8 hours at room temperature, LiCl produced during the reaction was removed by filtration, and the solvent was removed under a reduced pressure. The resultant compound in which two indenyls are alkylene bridged and bonded to trimethylsilane groups was obtained in 7.2 mmole. The yield of the compound is 80%. To the resultant compound was added a solution of TiCl$_4$ 14.5 mmole in 30 ml of dichloromethane at room temperature. After 10 hours, the solvent was removed under a reduced pressure to obtain a dark wine color solid. The solid was washed in 20 ml of hexane three times, recrystallized with dichloromethane and hexane to obtain IndTiCl$_3$-(CH$_2$)-IndTiCl$_3$ catalyst ("catalyst 1"). The yield of the catalyst was 65%

Example 2: snythesis of tetramethyldisilane-bis($\eta^5$-diindenyl-titaniumtrichloride): [IndTiCl$_3$-(Si(CH$_3$)$_2$)$_2$-IndTiCl$_3$]

After dissolving 10 mmole of 1,2-dichlorotetramethyldisilane in 100 ml of tetrahydrofuran (THF), to the solution were added butyl lithium and indene to produce white powder. The white powder 20 mmole was dissolved in 50 ml of TMF at −78° C., the solution was heated at room temperature, and then agitated for about 30 hours. To the solution as added 200 ml of diethylether and 100 ml of water to prepare a greasy type reaction mixture. To the mixture was added 50 ml of hexane, and a white powder ligand that two indenes were bridged was obtained in 85% of yield. To 8.5 mmole of the ligand compound was added 50 ml of hexane, 17 mmole of butyl lithium was added at −78° C., the solution was heated at room temperature, and then agitated for about 5 hours. A white powder dianion compound in which two indenyls are bonded to lithium atoms was prepared. After filtering the dianion compound, trimethylsilylchloride (TMSCl) was added in 100ml of hexane solvent, agitated for 8 hours at room temperature, LiCl produced during the reaction was removed by filtration, and the solvent was removed under a reduced pressure. The resultant compound in which two indenyls are alkylene bridged and bonded to trimethylsilane groups was obtained in 0.4 mmole. The yield of the compound is 75%. To the resultant compound was added a solution of TiCl$_4$ 13 mmole in 30 ml of dichloromethane at room temperature. After 10 hours, the solvent was removed under a reduced pressure to obtain a dark wine color solid. The solid was washed in 20 ml of hexane three times, recrystallized with dichloromethane and hexane to obtain IndTiCl$_3$-(Si(CH$_3$)$_2$)$_2$-IndTiCl$_3$ catalyst ("catalyst 2"). The yield of the catalyst was 50%.

Example 3: synthesis of [bis(dimethylsilyl)]butane-[bis($\eta^5$-diindenyl-titaniumtrichloride)]: [IndTiCl$_3$-Si(CH$_3$)$_2$-(CH$_2$)$_4$-Si(CH$_3$)$_2$-IndTiCl$_3$]

After dissolving 10 mmole of 1,4-bis (chlorodimethylsilyl)butane in 100 ml of tetrahydrofuran (THF), to the solution were added butyl lithium and indene to produce white powder. The white powder 20 mmole was dissolved in 50 ml of TMF at −78° C., the solution was heated at room temperature, and then agitated for about 20 hours. To the solution was added 200 ml of diethylether and 100 ml of water to prepare a greasy type reaction mixture. To the mixture was added 50 ml of hexane, and a white powder ligand that two indenes were bridged was obtained in 85% of yield. To 8.5 mmole of the ligand compound was added 50 ml of hexane, 17 mmole of butyl lithium was added at −78° C., the solution was heated at room temperature, and then agitated for about 8 hours. A white powder dianion compound in which two indenyls are bonded to lithium atoms was prepared. After filtering the dianion compound, trimethylsilylchloride (TMSCl) was added in 100 ml of hexane solvent, agitated for 8 hours at room temperature LiCl produced during the reaction was removed by filtration, and the solvent was removed under a reduced pressure. The resultant compound in which two indenyls are alkylene bridged and bonded to trimethylsilane groups was obtained in 6.4 mmole. The yield of the compound is 75%. To the resultant compound was added a solution of TiCl$_4$ 13 mmole in 30 ml of dichloromethane at room temperature. After 10 hours, the solvent was removed under a reduced pressure to obtain a dark wine color solid. The solid was washed in 20 ml of hexane three times, recrystallized with dichloromethane and hexane to obtain IndTiCl$_3$-Si(CH$_3$)$_2$-(CH$_2$)$_4$-Si(CH$_3$)$_2$)-IndTiCl$_3$ catalyst ("catalyst 3"). The yield of the catalyst was 40%.

Although Examples 1–3 illustrate binuclear metallocene catalysts containing two indenyls, catalysts containing any two groups selected from a cyclopentadienyl; an alkyl alkoxy, silyl or halogen substituted cyclopentadienyl; an alkyl, alkoxy, silyl or halogen substituted indenyl; a fluorenyl; and an alkyl, alkoxy, silyl or halogen substituted fluorenyl can be obtained in the same manner above.

Alkylene and/or silylene bridged hetero-bimetallic metallocene catalysts can be prepared by reacting $TiCl_4$, $ZrCl_4$ and $HfCl_4$ consecutively with the salt state compound of the bridged compound or a ligand having two trimethylsilanes. The following Examples 4–6 are to prepare hetero-bimetallic metallocene catalysts having Ti and Zr as binuclear metal.

Example 4; synthesis of butane-bis($\eta^5$-cyclopentadienyltitanium-trichloride) ($\eta^5$-cyclopentadienylzirconiumtrichloride): [$CpTiCl_3$-$(CH_2)_4$-$CpZrCl_3$]("catalyst 4")

Example 4 was performed as in Example 1 with the exceptions that cyclopentadiene was employed instead of indene, and that $TiCl_4$ and $ZrCl_4$ were consecutively employed instead of $TiCl_4$.

Example 5: synthesis of tetramethyldisilane ($\eta^5$-cyclopentadienyl-titaniumtrichloride) ($\eta^5$-cyclopentadienylzirconiumtrichloride): [$CpTiCl_3$-$(Si(CH_3)_2)_2$-$CpZrCl_3$]("catalyst 5")

Example 5 was performed as in Example 2 with the exceptions that cyclopentadiene was employed instead of indene, and that $TiCl_4$ and $ZrCl_4$ were consecutively employed instead of $TiCl_4$.

Example 6: synthesis of bis(dimethylsilyl)butane($\eta^5$-cyclopenta-dienyltitaniumtrichloride) ($\eta^5$-cyclopentadienyl-zirconiumtrichloride): [$CpTiCl_3$-$Si(CH_3)_2$-$(CH_2)_2$-$Si(CH_3)_2$-$CpZrCl_3$]("catalyst 6")

Example 6 was performed as in Example 3 with the exceptions that cyclopentadiene was employed instead of indene, and that $TiCl_4$ and $ZrCl_4$ were consecutively employed instead of $TiCl_4$.

Example A: homopolymerization of styrene

Homopolymerization of styrene was carried out using the alkylene and/or silylene bridged binuclear metallocene catalysts prepared in Examples 1–6. Styrene was polymerized using a glass reactor equipped with a temperature controlled apparatus, a magnetic agitator and valves for supplying monomers and nitrogen. A purified toluene and MMAO as co-catalyst were put into a nitrogen-substituted reactor, mixed and stirred sufficiently. Styrene was added to the reactor. The alkylene and/or silylene bridged binuclear metallocene catalyst was added to the reactor and polymerization was carried out. The polymerization was terminated by adding ethanol. Syndiotactic polystyrene was obtained by adding $HCl/CH_3OH$ solution to the resultant, washing with water and methanol, and vacuum-drying. In the polymerization of styrene, the ratio of [Al] to [Ti] was 1,000:1, the polymerization temperature was 40' C., and the content of styrene was 1.0 mole/l.

The following Table 1 sets forth catalyst activity, stereoregularity, melting point, molecular weight and molecular weight distribution in accordance with the catalysts of Examples 1–6.

Example B: copolymerization of styrene

Example B was performed as in Example A with the exception that 1.0 mole/l of styrene and 6% by weight of para-methylstyrene per the styrene were employed instead of 1.0 mole/l of styrene.

The following Table 2 sets forth catalyst activity, melting point, molecular weight and molecular weight distribution in accordance with the catalysts of Examples 1–6.

Example C: terpolymerization of styrene

Example C was performed as in Example A with the exception that 1.0 mole/l of styrene, 6% by weight of para-methylstyrene per the styrene and 2% by weight of polybutadiene per the styrene were employed instead of 1.0 mole/l of styrene.

The following Table 3 sets forth catalyst activity, melting point, molecular weight and molecular weight distribtuion in accordance with the catalysts of Examples 1–6.

Comparative Examples A1, B1 and C1

Examples A1, B1 and C1 were performed as in Examples A, B and C, respectively, with the exception that cyclopentadienyl-titaniumtrichloride ($CpTiCl_3$) was employed as catalyst.

The physical properties for Comparative Examples A1, B1 and C1 are shown in Tables 1, 2 and 3, respectively.

Comparative Examples A2, B2 and C2

Examples A2, B2 and C2 were performed as in Examples A, B amd C, respectively, with the exception that pentamethylcyclopentadienyltitaniumtrichloride ($Cp^*TiCl_3$) was employed as catalyst.

The physical properties for Comparative Examples A2, B2 and C2 are shown in Tables 1, 2 and 3, respectively.

Comparative Examples A3, B3 and C3

Examples A3, B3 and C3 were performed as in Examples A, B and C, respectively, with the exception that indenyltitaniumtrichloride ($IndTiCl_3$) was employed as catalyst.

The physical properties for Comparative Examples A3, B3 and C3 are shown in Tables 1, 2 and 3, respectively.

TABLE 1

| | | catalyst | homopolymerization | | | | |
| --- | --- | --- | --- | --- | --- | --- | --- |
| | | | catalyst activity | stereo-regularity | melting point (° C.) | molecular weight ($\times 10^{-3}$) | molecular weight distribution |
| Example A | | catalyst 1 | 5,000 | 97.5 | 271 | 280 | 3.5 |
| | | catalyst 2 | 3,800 | 96.0 | 270 | 250 | 3.5 |
| | | catalyst 3 | 3,500 | 96.0 | 270 | 200 | 3.5 |
| | | catalyst 4 | 1,200 | 93.0 | 270 | 110 | 3.0 |
| | | catalyst 5 | 1,000 | 92.0 | 270 | 100 | 3.2 |
| | | catalyst 6 | 1,000 | 91.0 | 269 | 100 | 3.5 |
| Comparative | A1 | $CpTiCl_3$ | 1,500 | 86.0 | 268 | 110 | 2.6 |
| Example | A2 | $IndTiCl_3$ | 3,500 | 93.0 | 270 | 210 | 2.4 |
| | A3 | $Cp^*TiCl_3$ | 5,000 | 94.0 | 270 | 250 | 2.3 |

TABLE 2 copolymerization

| | | catalyst | catalyst activity | melting point (° C.) | molecular weight (× 10⁻³) | molecular weight distribution |
|---|---|---|---|---|---|---|
| Example B | | catalyst 1 | 4,000 | 245 | 180 | 2.57 |
| | | catalyst 2 | 2,500 | 244 | 150 | 2.55 |
| | | catalyst 3 | 1,500 | 243 | 150 | 2.34 |
| | | catalyst 4 | 1,200 | 244 | 130 | 2.54 |
| | | catalyst 5 | 900 | 242 | 100 | 3.21 |
| | | catalyst 6 | 900 | 243 | 110 | 3.23 |
| Comparative | B1 | CpTiCl₃ | 1,300 | 242 | 110 | 2.76 |
| Example | B2 | IndTiCl₃ | 2,300 | 243 | 150 | 1.88 |
| | B3 | Cp*TiCl₃ | 4,100 | 243 | 170 | 1.75 |

TABLE 3 terpolymerization

| | | catalyst | catalyst activity | melting point (° C.) | molecular weight (× 10⁻³) | molecular weight distribution |
|---|---|---|---|---|---|---|
| Example C | | catalyst 1 | 4,200 | 227 | 250 | 2.33 |
| | | catalyst 2 | 3,500 | 230 | 230 | 2.34 |
| | | catalyst 3 | 1,500 | 228 | 200 | 2.35 |
| | | catalyst 4 | 1,300 | 229 | 150 | 2.33 |
| | | catalyst 5 | 1,000 | 227 | 110 | 2.33 |
| | | catalyst 6 | 1,000 | 228 | 100 | 2.34 |
| Comparative | C1 | CpTiCl₃ | 1,500 | 226 | 110 | 1.95 |
| Example | C2 | IndTiCl₃ | 3,100 | 227 | 200 | 1.92 |
| | C3 | Cp*TiCl₃ | –4,500 | 227 | 220 | 1.91 |

The stereoregularity of catalysts in Table 1 was analyzed with $^1$H-NMR and $^{13}$C-NMR.

The catalyst activity (kg PS/[Ti][St]hrs) in Tables 1, 2 and 3 was obtained by measuring the weight of the syndiotactic polystyrene prepared.

The stereoregularity in Table 1 was obtained in percent (%) by measuring the weight of the polymer which was extracted with methylethylketone, corresponding to syndioactic index (S.I.).

The melting point and crystallization temperature in Tables 1, 2 and 3 were obtained using the Du Pont 2000 System (Differential Scanning Calorimetry: DSC). The test sample was heated to 200° C. and maintained for cooling for 5 minutes. The temperature rate was 10° C./min.

As shown in Tables 1–3, the catalyst activities of Examples 1–3 are much higher than those of Comparative Examples A1, B1 and C1, same or higher than those of Comparative Examples A2, B2 and C2, but same or lower than those of Comparative Examples A3, B3 and C3. However, the stereoregularities (S.I.) of Examples 1–3 are higher than those of Comparative Examples A1, A2 and A3. The melting points of the homopolymer, copolymer and terpolymer are about 270° C., 244° C. and 227° C., respectively. In case of using catalysts 1–3, molecular weight distributions are broader than those of the Comparative Examples, but molecular weights are higher as a whole.

In regard to catalysts 4–6 of Examples 4–6, the catalyst activities are almost same as those of Comparative Examples A1, B1 and C1, and lower than those of Comparative Examples A2, B2, C2, A3, B3 and C3. The stereoregularities (S.I.) of Examples 4–6 are superior to Comparative Example A1, but similar to those of Comparative Examples A2 and A3. The melting points of the homopolymer, copolymer and terpolymer according to Examples 4–6 are about 270° C., 244° C. and 227° C., respectively. In case of using catalysts 4–6, molecular weight distributions are broader than those of the Comparative Examples, but molecular weights are similar as a whole.

Consequently, the alkylene and/or silylene bridged binuclear metallocene catalysts according to this invention are capable of preparing a syndioactic polystyrene having more stereoregularity and higher melting point and crystallization temperature than the conventional metallocene catalysts.

Further modifications of the invention will be apparent to those skilled in the ant and all such modifications are deemed to be with the scope of the invention as defined in the following claims.

What is claimed is:

1. An alkylene and/or silylene bridged binuclear metallocene catalyst for styrene polymerization, represented by the following formula (I):

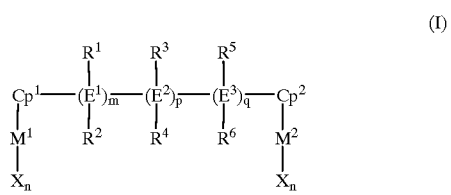

wherein $M^1$ and $M^2$ are the same or different transition metal of Group IVb of the Periodic Table; $Cp^1$ and $Cp^2$ are the same or different cyclopentadienyl; alkyl, aryl, alkoxy, silyl, aryloxy, siloxy or halogen substituted cyclopentadienyl; indenyl; alkyl, aryl, alkoxy, silyl, aryloxy, siloxy or halogen substituted indenyl; fluorenyl; or alkyl, aryl, alkoxy, silyl, aryloxy, siloxy or halogen substituted fluorenyl, which is capable of π-electron, $\eta^5$-bonding with $M^1$ or $M^2$; each of $E^1$, $E^2$ and $E^3$, independently of one another, is a carbon atom or a silicon atom; m, p and q are integers of 0 to 15 and $3 \leq m+p+q \leq 12$; each of $R^1$, $R^2$, $R^3$, $R^4$, $R^5$ and $R^6$, independently of one another, is a hydrogen, an alkyl, an aryl, an alkoxy or a halogen; X is a hydrogen, an alkyl, an alkoxy or a halogen; and n is 3.

2. The metallocene catalyst as in claim 1 wherein said metallocene catalyst is supported on a support.

3. The metallocene catalyst as in claim 2 wherein said support is selected from the group consisting of silica, alumina, magnesium chloride, a zeolite, aluminum phosphate and zirconia.

4. The metalllocene catalyst as in claim 2 wherein said support is activated and contains a non-aluminum co-catalyst or an organometallic compound.

5. The metallocene catalyst as in claim 4 in which said non-aluminum co-catalyst is selected from the group consisting of $[R^7R^8R^9C]^+[BQ_1Q_2Q_3Q_4]^{31}$ and $[NHR^{10}R^{11}R^{12}]^+[BQ_1Q_2Q_3Q_4]^-$, wherein $R^7 \sim R^{12}$, independently of one another, are a hydrogen, an alkyl, an aryl, alkoxy, a silyl or a siloxy, B is a boron having +3 valence, and each of $Q_1$, $Q_2$, $Q_3$ and $Q_4$, independently of one another, is a radical selected from the group consisting of a hydride, a dialkylamido, an alkoxide, an aryl oxide and a hydrocarbyl.

6. An alkylene and/or silylene bridged binuclear metallocene catalyst for styrene polymerization, represented by the following formula (II):

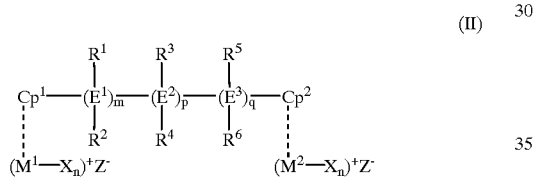

(II)

wherein $M_1$ and $M^2$ are the same or different transition metal of Group IVb of the Periodic Table; $Cp^1$ and $Cp_2$ are the same or different cyclopentadienyl; alkyl, aryl, alkoxy, silyl, aryloxy, siloxy or halogen substituted cyclopentadienyl; indenyl; alkyl, aryl, alkoxy, silyl, aryloxy, siloxy or halogen substituted indenyl; fluorenyl; or alkyl, aryl, alkoxy, silyl, aryloxy, siloxy or halogen substituted fluorenyl, which is capable of π-electron, $\eta^5$-bonding with $M^1$ and $M^2$; each of $E^1$, $E^2$ and $E^3$, independently of one another, is a carbon atom or a silicon atom; m, p and q are integers of 0 to 15 and $3 \leq m+p+q \leq 12$; each of $R^1$, $R^2$, $R^3$, $R^4$, $R^5$ and $R^6$, independently of one another, is a hydrogen, an alkyl, an aryl, an alkoxy or a halogen; X is a hydrogen, an alkyl, an alkoxy or a halogen; n is 2; and Z is a non-coordinating anion represented by the formula $[BQ_1Q_2Q_3Q_4]$; wherein B is a boron having +3 valence, and each of $Q_1$, $Q_2$, $Q_3$ and $Q_4$, independently of one another, is a radical selected from the group consisting of a hydride, a dialkylamido, an alkoxide, an aryl oxide and a hydrocarbyl.

7. A process for preparing an alkylene and/or silylene bridged binuclear metallocene catalyst represented by the following formula (I):

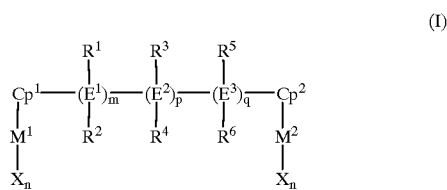

(I)

wherein $M_1$ and $M^2$ are the same or different transition metal of Group IVb of the Periodic Table; $Cp^1$ and $Cp^2$ are the same or different cyclopentadienyl; alkyl, aryl, alkoxy, silyl, aryloxy, siloxy or halogen substituted cyclopentadienyl; indenyl; alkyl, aryl, alkoxy, silyl, aryloxy, siloxy or halogen substituted indenyl; fluorenyl; or alkyl, aryl, alkoxy, silyl, aryloxy, siloxy or halogen substituted fluorenyl, which is capable of π-electron, $\eta^5$-bonding with $M^1$ and $M^2$; each of $E^1$, $E^2$ and $E^3$, independently of one another, is a carbon atom or a silicon atom; m, p and q are integers of 0 to 15 and $3 \leq m+p+q \leq 12$; each of $R^1$, $R^2$, $R^3$, $R^4$, $R^5$ and $R^6$, independently of one another, is a hydrogen, an alkyl, an aryl, an alkoxy or a halogen; X is a hydrogen, an alkyl, an alkoxy or a halogen; n is 3, comprising the steps of:

(1) providing an alkali metal compound of an $\eta^5$-bonding, π-electron cyclopentadienyl; an alkyl, alkoxy, silyl or halogen substituted cyclopentadienyl; an indenyl; an alkyl, alkoxy, silyl or halogen substituted indenyl; a fluorenyl; or an alkyl, alkoxy, silyl or halogen substituted fluoroenyl;

(2) reacting the alkali metal compound with a dihalide alkylene compound, a dihalide silylene compound or a dihalide alkylene-silylene compound, thereby producing an alkylene bridged compound, a silylene bridged compound, or an alkylene-silylene bridged compound of same or different two groups of a cyclopentadienyl; an alkyl, alkoxy, silyl or halogen substituted cyclopentadienyl; an indenyl; an alkyl, alkoxy, silyl or halogen substituted indenyl; a fluorneyl; or an alkyl, alkoxy, silyl or halogen substituted fluorneyl;

(3) reacting the bridged compound with an alkali metal or thallium compound having an alkyl or alkoxy group, thereby producing a salt of the bridged compound; and (4) reacting the salt of the bridged compound with a group 4 halide compound.

8. The process as in claim 7, wherein the salt of the bridged compound is reacted in step (4) with titanium tetrachloride, zirconium tetrachloride or hafnium tetrachloride.

9. The process as in claim 7 which further comprises a step of adding trimethylsilyl chloride to the salt of the bridged compound before the salt of the bridged compound is reacted with said group 4 halide compound.

10. The process as in claim 7, further comprising the step of:

(5) bonding a non-coordinating anion to the transition metal of the group 4 halide compound.

* * * * *